(12) United States Patent
Reddavide et al.

(10) Patent No.: US 11,365,439 B2
(45) Date of Patent: Jun. 21, 2022

(54) METHOD FOR IDENTIFYING HIGH-AFFINITY COMPLEXES MADE OF TWO LIGANDS AND ONE RECEPTOR, DEVICE FOR IMPLEMENTING THE METHOD AND SELF-ASSEMBLING CHEMICAL LIBRARY FOR USE IN THE METHOD

(71) Applicant: TECHNISCHE UNIVERSITAET DRESDEN, Dresden (DE)

(72) Inventors: Francesco Reddavide, Dresden (DE); Helena De Andrade, Dresden (DE); Weilin Lin, Dresden (DE); Yixin Zhang, Dresden (DE)

(73) Assignee: DYNABIND GMBH, Dresden (DE)

( * ) Notice: Subject to any disclaimer, the term of this patent is extended or adjusted under 35 U.S.C. 154(b) by 113 days.

(21) Appl. No.: 15/326,172

(22) PCT Filed: Jul. 10, 2015

(86) PCT No.: PCT/EP2015/065874
§ 371 (c)(1),
(2) Date: Jan. 13, 2017

(87) PCT Pub. No.: WO2016/008822
PCT Pub. Date: Jan. 21, 2016

(65) Prior Publication Data
US 2017/0198336 A1    Jul. 13, 2017

(30) Foreign Application Priority Data
Jul. 16, 2014   (DE) .................... 10 2014 213 783.7

(51) Int. Cl.
| | | |
|---|---|---|
| *C12Q 1/68* | (2018.01) | |
| *C12Q 1/6811* | (2018.01) | |
| *B01L 7/00* | (2006.01) | |
| *B01L 3/00* | (2006.01) | |
| *G01N 33/53* | (2006.01) | |

(52) U.S. Cl.
CPC .......... *C12Q 1/6811* (2013.01); *B01L 3/5027* (2013.01); *B01L 7/525* (2013.01); *G01N 33/5308* (2013.01); *B01L 2300/0681* (2013.01); *B01L 2300/088* (2013.01); *B01L 2300/0816* (2013.01); *B01L 2300/1822* (2013.01); *B01L 2300/1861* (2013.01); *B01L 2300/1894* (2013.01); *B01L 2400/0487* (2013.01)

(58) Field of Classification Search
CPC ................................ C12Q 1/68; C12Q 1/6811
See application file for complete search history.

(56) References Cited

U.S. PATENT DOCUMENTS

| | | | | |
|---|---|---|---|---|
| 5,512,439 | A * | 4/1996 | Hornes | C12N 15/102 435/6.11 |
| 7,018,793 | B1 * | 3/2006 | Short | C12N 9/00 435/183 |
| 2005/0009050 | A1 * | 1/2005 | Nadeau | C12Q 1/6804 435/6.18 |
| 2010/0159455 | A1 | 6/2010 | Landsman et al. | |
| 2010/0209925 | A1 * | 8/2010 | Ishibashi | B01L 3/5027 435/6.16 |
| 2011/0086361 | A1 * | 4/2011 | Klunder | C12Q 1/6834 435/6.12 |
| 2011/0111968 | A1 | 5/2011 | Okura et al. | |
| 2011/0319278 | A1 * | 12/2011 | Neri | C07H 21/00 506/9 |
| 2012/0115751 | A1 * | 5/2012 | Winssinger | C40B 40/06 506/9 |
| 2012/0308997 | A1 * | 12/2012 | Ruan | G01N 21/6456 435/6.1 |
| 2015/0159195 | A1 | 6/2015 | Leclipteux et al. | |

FOREIGN PATENT DOCUMENTS

| | | |
|---|---|---|
| JP | 2000-510136 | 8/2000 |
| JP | 2010-503860 | 2/2010 |
| WO | WO 9743232 A1 | 11/1997 |
| WO | WO 02/081729 A2 | 10/2002 |
| WO | 03/076943 | 9/2003 |
| WO | WO 03/076943 A1 | 9/2003 |
| WO | WO 2008/036273 A2 | 3/2008 |
| WO | 2010/150103 | 12/2010 |
| WO | WO 2010/150103 A2 | 12/2010 |
| WO | WO 2014005969 A1 | 1/2014 |

OTHER PUBLICATIONS

Attie et al., Analysis of Receptor-Ligand Interactions, Journal of Chemical Education, 72(2), 1995, 119-124. (Year: 1995).*
Reddavide et al., DNA-Encoded Dynamic Combinatorial Chemical Libraries, Angew. Chem. Int. Ed., 2015, 54, 7924-7928. (Year: 2015).*
Reddavide et al., Supporting Information, DNA-Encoded Dynamic Combinatorial Chemical Libraries, Angew. Chem. Int. Ed., 2015, 54, 7924-7928. (Year: 2015).*
Kollmann et al., Application of Encoded Library Technology (ELT) to a Protein-Protein Interaction Target: Discovery of a Potent Clas of Integrin Lymphocyte Function-Associated Antigen 1 (LFA-1) Antagonists, Bioorganic Medicinal Chemistry, 2014, 22, 2535-2365. (Year: 2014).*

(Continued)

Primary Examiner — Amy M Bunker
(74) Attorney, Agent, or Firm — Jacobson Holman PLLC (57) ABSTRACT

The present invention relates to a method for the sensitive identification of high-affinity complexes made of two ligands (2, 3, 4, 5, 6, 7) and one receptor (1). A large number of different ligands (2, 3, 4, 5, 6, 7) of a chemical library are hereby contacted with at least one receptor (1) in a solution. The ligands of the library have a single-strand DNA (8, 9) or RNA with a base length of 2 to 10 bases or alternatively more than 10 bases. In addition, the solution is incubated for a specific period of time and complexes made of two ligands (2, 3, 4, 5, 6, 7) and one receptor (1) are identified.

12 Claims, 6 Drawing Sheets

(56) References Cited

OTHER PUBLICATIONS

Franzini et al., DNA-Encoded Chemical Libraries: Advancing Beyond Conventional Small-Molecule Libraries; Accounts of Chemical Research, 2014, 47, 1247-1255. (Year: 2014).*
Melkko et al., Encoded Self-Assembling Chemical Libraries, Nature Biotechnology, 2004, 22, 568-574. (Year: 2004).*
Merriam-Webster, Dissociate, Merriam-Webster Dictionary, 2021, 1-2. Obtained online at: https://www.merriam-webster.com/dictionary/dissociate on Jul. 22, 2021. (Year: 2021).*
Hofstadler et al., Applications of ESI-MS In Drug Discovery: Interrogation of Non-Covalent Complexes, Nature Reviews/Drug Discovery, 2006, 5, 585-595. (Year: 2006).*
M. Ciobanu et al., "Selection of a synthetic glycan oligomer from a library of DNA-templated fragments against DC-SIGN . . . ", Chem Comm., vol. 47, No. 33, Jul. 25, 2011, pp. 9321-9323.
Daguer et al., "DNA-Templated Combinatorial Assembly of Small Molecule Fragments Amenable to Selection/Amplification Cycles, "Chem. Sci., 2011, 2, 625-632.
R. Franzini et al., "DNA-Encoded Chemical Libraries: Advancing beyond Conventional Small-Molecule Libraries", Accounts of Chemica Res., vol. 47, No. 4, pp. 1247-1255 (Mar. 28, 2014).
N. Svensen et al., "Decoding a PNA Encoded Peptide Library by PCR: The Discovery of New Cell Surface Receptor Ligands", Chem. Biol. (2011) vol. 18, pp. 1284-1289.
N. Winssinger, DNA display of PNA-tagged ligands. Artificial DNA: PNA & XNA, vol. 3:3, pp. 105-108 (2012).
Scheuermann et al. Dual-pharmacophore DNA-encoded chemical libraries. Current Opinion in Chemical Biology. 28:99-103, Mar. 13, 2015.
Scheuermann et al., DNA-encoded chemical libraries for the discovery of MMP-3 inhibitors. Bioconjugate Chemistry, vol. 19, No. 13, pp. 778-786, Mar. 1, 2008.
Mannocci et al. 20 years of DNA-encoded chemical libraries. Chemical Communications, vo. 47, No. 48, Dec. 28, 2011, pp. 12747-12753.
Buller et al. Drug discovery with DNA-encoded chemical libraries. Bioconjugate Chemistry, vol. 21, No. 9, Sep. 15, 2010, pp. 1571-1580.
Sprinz et al. Self-assembly of bivalent protein-binding agents based on oligonucleotide-linked organic fragments. Bioorg.Med. Chem, Letter 15 (2005), p. 3908-3911.
Reddavide et al. DNA-Encoded Dynamic Combinatorial Chemical Libraries. Angew. Chem. Int. Ed. 54, May 26, 2015, p. 7924-7928.
Canadian Office Action.
Japanese Office Action and English Translation.

* cited by examiner

METHOD FOR IDENTIFYING HIGH-AFFINITY COMPLEXES MADE OF TWO LIGANDS AND ONE RECEPTOR, DEVICE FOR IMPLEMENTING THE METHOD AND SELF-ASSEMBLING CHEMICAL LIBRARY FOR USE IN THE METHOD

A method for identifying high-affinity complexes made of two ligands and one receptor is proposed. In the method, ligands of a library which have respectively a single-strand DNA or RNA are used. Since the DNA or RNA of one part of the ligands is complementary to the DNA or RNA of another part of the ligands, both parts of the ligands together can form binary complexes. The length of the DNA or RNA, in one embodiment, can be 3 to 10 bases or, in another embodiment, more than 10 bases. According to the invention, hybridisation and dissociation of the single-strand DNAs or RNAs is provided in a dynamic manner which is achieved in fact at room temperature for the first embodiment and, for the second embodiment, a cycle of heating and cooling is required. Furthermore, a microfluidic device for implementing the method according to the invention and a dynamic, self-assembling chemical library comprising binary complexes of the respective ligands is proposed.

An essential requirement in the use of DNA-coded chemical libraries and DNA/RNA aptamer libraries for finding effective binders and inhibitors relative to various target proteins of biomedical interest is improving the signal-to-noise ratio in selection experiments in order to distinguish molecules with high binding affinity from weak or non-binding compounds.

To date, in the prior art generally parallel selection experiments with differing selection stringency have been implemented in order to optimise the selection conditions relative to a known target protein. For example solid carrier materials were thus charged with different quantities of the target protein. Furthermore, various washing methods were established, in which buffers with different ion strengths and detergents were used.

In order to implement parallel selection experiments, many additional experiments for a target protein must be implemented. This is both time-consuming and expensive. In addition, it is very difficult to design parallel selection experiments with varying stringency in the selection if the distributions of the binding affinities of the entire library for the target protein are unknown. In order to select binders with high affinity, special selection conditions must be applied. Accordingly, it is a disadvantage that a stringent, parallel selection experiment can only be designed after it is known that high-affinity binding molecules are located in the library.

On the other hand, also the characterisation of components of a first selection experiment (de novo selection experiment) is very time-consuming and costly. In addition, it is difficult to design a parallel selection experiment without the knowledge and the information resulting from a preceding primary selection.

The object of the present invention is hence the provision of a method with which, in a simple, economical and highly-sensitive manner, identification of high-affinity ternary complexes made of two ligands and one receptor is possible. In addition, a device for implementing the method and a self-assembling chemical library for use in the method should be provided.

The object is achieved by the method, the dynamic self-assembling chemical library, and the use of the library as described and claimed below.

According to the invention, a method for sensitive identification of high-affinity complexes made of two ligands and one receptor is provided, which comprises the following steps:

a) interaction of a large number of different complexes made of ligands of a chemical library with at least one receptor in a solution, the ligands of the library having a single-strand DNA or RNA with a base length of more than 10 bases, which is bonded chemically covalently to the ligands, and more than 10 bases of the single-strand DNA or RNA of a first part of the ligands being complementary to bases of the single-strand DNA or RNA of a second part of the ligands, and the ligands being complexed to form ligand complexes via hybridisation of the DNA or RNA;

b) incubation of the solution for a specific period of time, complexes made of ligand complexes and the receptor being produced;

c) dissociation of the ligand complexes to form free ligands;

d) re-hybridisation of the free ligands to form further ligand complexes;

e) incubation of the solution for a specific period of time, further complexes made of the further ligand complexes and the receptor being produced;

f) identification of the resulting complexes made of ligand complexes and the receptor.

The method is characterised in that incubation takes place at a temperature (step b), step d) and/or step e)) at which the first part of the ligands and the second part of the ligands are hybridised in the solution to form ligand complexes.

In the presence of a receptor which has high-affinity to a specific combination of two ligands (specific binary ligand complex made of ligand 1 and ligand 2 via dsDNA or dsRNA), a high-affinity ternary ligand-receptor complex made of the two ligands and the receptor is formed. High-affinity ligand pairs are hence depleted in the pool of binary ligand pairs and enriched in the form of a ternary ligand pair-receptor complex.

The disadvantage of methods from the state of the art is that a specific percentage of high-affinity ligands with few as far as absolutely no affine ligands is hybridised and hence is "trapped" in low-affinity ligand complexes. This problem is resolved by the method according to the invention. By means of a method step in which ligand pairs are specifically dissociated, the high-affinity ligands "trapped" previously in the ligand complex become "free" again in order to hybridise, in a further hybridisation step of the method, with other free high-affinity ligands to form new ligand complexes. The newly formed ligand complexes are in turn available for forming ligand-receptor complexes. As a result, the high-affinity ligands—in the ideal case quantitatively—can hence be specifically converted into ligand-receptor complexes, which produces a larger quantity of ligand-receptor complexes and hence increases the sensitivity of the method relative to methods from the state of the art (improved signal-to-noise ratio). In fact, the frequency of the formation of the high-affinity ligand pair, in the case of a number of N theoretically possible high-affinity ligand pairs in a library, can be increased ideally up to a factor N (quantitative formation of high-affinity complexes, no high-affinity ligands are bonded to low-affinity ligands and hence "trapped").

The ligand complexes can be dissociated for example by increasing the temperature of the solution, in particular to a temperature of 35° C. to 95° C., preferably 50° C. to 95° C., particularly preferably 70° C. to 95° C., in particular 80° C. to 95° C.

The dissociation of the ligand complexes is preferably implemented in a part of the solution which is spatially at a spacing from the receptor, preferably such that the receptor is not functionally impaired by the conditions which lead to the dissociation. The advantage of this embodiment is that the effect of the dissociation does not have a negative effect on the (biological) function of the receptor. In particular, receptors are consequently protected from thermal and/or pH-induced denaturation (e.g. receptors which comprise proteins or consist thereof).

The free ligands can (again) be hybridised by lowering the temperature of the solution, in particular by lowering to a temperature of 1° C. to 30° C., preferably 5° C. to 28° C., particularly preferably 10° C. to 25° C., in particular 15° C. to 20° C.

Steps c) to e) of the method can be repeated at least once or twice, preferably at least 3 or 4 times, particular preferably at least 5 or 6 times, in particular at least 7 or 8 times. The more often the steps are repeated, the more are high-affinity ligand complexes gradually converted into the ligand-receptor complex (rise in sensitivity).

In a preferred embodiment, at least 20 bases, preferably at least 40 bases, particularly preferably a least 100 bases, in particular at least 200 bases, of the single-strand DNA or RNA of a first part of the ligands are complementary to the single-strand DNA or RNA of a second part of the ligands.

Furthermore, an alternative solution to the object according to the invention is provided, which solution is possible without heating and cooling steps.

In this respect, a method for sensitive identification of high-affinity complexes made of two ligands and one receptor is provided, which comprises the following steps:
i) interaction of a large number of different complexes made of ligands of a chemical library with at least one receptor in a solution, the ligands of the library having a single-strand DNA or RNA with a base length of more than 2 bases, which is bonded chemically covalently to the ligands, and only 2 to 10 bases of the single-strand DNA or RNA of a first part of the ligands being complementary to bases of the single-strand DNA or RNA of a second part of the ligands, and the ligands being complexed to form ligand complexes via hybridisation of the DNA or RNA;
ii) incubation of the solution for a specific period of time, complexes made of ligand complexes and the receptor being produced; and
iii) identification of the resulting complexes made of ligand complexes and the receptor.

The method is characterised in that the solution is incubated at a temperature at which, between the first part of the ligands and the second part of the ligands, an equilibrium of hybridisation to form ligand complexes and dissociation to form free ligands arises (e.g. room temperature, i.e. 15° C. to 30° C.). As a result, a dynamic hybridisation and dissociation is obtained.

The difference from the first-mentioned method according to the invention is that, by means of the lower number of complementary bases between the two parts of the ligands, association (via hybridisation) and dissociation of the ligands takes place in fact at room temperature (dynamic equilibrium). By means of the presence of a receptor, high-affinity ligand pairs are "withdrawn" from the dynamic equilibrium and converted into the ligand-receptor complex. High-affinity ligand pairs are therefore depleted in the general ligand pool of the chemical library and the high-affinity, ternary ligand-receptor complex is enriched. By means of the dynamic equilibrium, all high-affinity ligand pairs (in the ideal case quantitatively) are therefore converted into the receptor complex even without heating and cooling, which increases the concentration of ligand-receptor complexes and hence improves the sensitivity of the detection method. The disadvantage however is an overall somewhat low affinity of the ligand pairs for the receptor compared with the ligand pairs from the first-mentioned method since the stability of the ligand pairs is somewhat less due to the lower number of complementary bases and hence, in equilibrium, also the ternary ligand-receptor complex is populated less highly.

In this variant, only 3 to 9 bases, preferably only 4 to 8 bases, particularly preferably only 5 to 7 bases, of the single-strand DNA or RNA of a first part of the ligands can be complementary to the single-strand DNA or RNA of a second part of the ligands.

In both methods, the length of the DNA or RNA of the first part of the ligands and/or second part of the ligands can be at least 20 bases, preferably at least 40 bases, particularly preferably at least 100 bases, in particular at least 200 bases.

The first and/or second part of the ligands can constitute more than 20%, preferably more than 30%, particularly preferably more than 40%, in particular 50%, of the total quantity of the ligands. The first part of the ligands preferably has L different ligands and the second part of the ligands preferably has M different ligands so that L·M different binary ligand complexes are formed. For a library with L·M binary ligand complexes, a specific high-affinity ligand complex can be enriched with increased efficiency of at least 1.5 to N times, preferably 2 to $N^{(1/2)}$ times, in particular 3 to 10 times.

In a preferred embodiment, the solution is incubated in at least one of steps b), e) and ii) at a temperature of 1° C. to 50° C. preferably 5° C. to 37° C., particularly preferably 10° C. to 25° C., in particular 15° C. to 20° C. At these temperature ranges, it is advantageous that many types of receptor (in particular protein receptors) are stable here and have not lost their function of binding ligands.

The solution can be incubated in at least one of steps b), e) and ii) for a period of time of 0.1 to 48 hours, preferably 0.2 to 24 hours, particularly preferably 0.5 to 12 hours, in particular 1 to 6 hours. Fairly long incubation times have proved to be advantageous since the binding of the ligand pairs to the receptor can in fact be assisted thermodynamically but nevertheless can have slow kinetics.

The receptor which is used in the methods according to the invention can be immobilised, preferably on a substrate selected from the group consisting of glass, ceramic, biopolymer, sepharose, synthetic polymer and hydrogel. In particular, the solution with ligands can hereby be guided past the immobilised receptor in a cycle. This embodiment is advantageous if, in the method, the dissociation of the ligand complexes is implemented in one part of the solution which is spatially at a spacing from the receptor since dissociation and hybridisation of the ligands can in fact be separated hereby spatially but nevertheless take place at the same time (e.g. dissociation at a distance from the receptor, hybridisation close to the receptor).

The receptor preferably comprises a protein, a DNA, an RNA, a cell and/or an organic molecule with a molecular mass≤200 kDa, preferably ≤100 kDa, particularly preferably ≤10 kDa, in particular ≤3 kDa, or consists thereof.

The ligands used can comprise a molecule selected from the group consisting of protein, peptide, lipid, carbohydrate, dsDNA, ssDNA, dsRNA and ssRNA, aptamer, organic molecule with a molecular mass≤200 kDa, preferably ≤100 kDa, particularly preferably ≤10 kDa, in particular ≤3 kDa, or consist thereof.

In a preferred embodiment, the complexes made of ligand complexes and the receptor are identified via an analytical method. The method is preferably selected from the group consisting of mass spectrometry, HPLC, gas chromatography, IR spectroscopy and DNA sequencing, preferably DNA sequencing of a DNA- or RNA barcode.

Further preferably, the single-strand DNA or RNA in the first and/or second part of the ligands comprises a base sequence which codes for the chemically covalently-bonded ligand (base sequence as barcode), this base sequence preferably being hybridised to form a complementary base sequence of a further single-strand DNA or RNA. The advantage of the barcode resides in simple identification of complex-bonded ligands via DNA—or RNA sequencing. It is particularly advantageous if the base sequence of the ligands comprises a complementary single-strand DNA- or RNA, hybridised, which can serve likewise as barcode. If both ligands of the ligand-receptor complex (ligand 1 and 2) comprise a single-strand DNA or RNA, then these can be ligated, e.g. by addition of a ligase, a single-strand DNA- or RNA being obtained which codes for the specific combination of ligand 1 and 2. The (ligated) barcode in this case codes therefore not only for an individual ligand but for two ligands which together form a high-affinity ligand complex.

The single-strand DNA used in the method can comprise
i) adenine, thymine, guanine and/or cytosine; and/or
The single-strand RNA used in the method can comprise
ii) adenine, uracil, guanine, cytosine and/or inosine.

Figure 6:
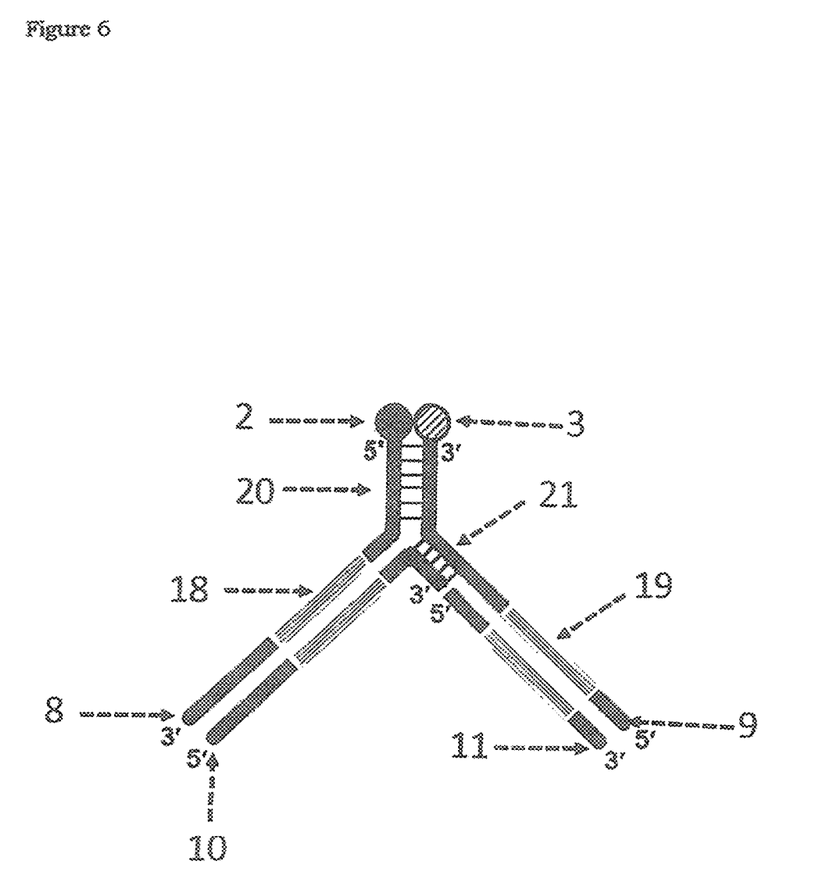

The method is characterised, in an advantageous embodiment, in that the single-strand DNA or RNA of the ligands of the library is hybridised in regions to form a complementary base sequence of a further single-strand DNA or RNA, 2 to 10 bases of the further single-strand DNA or RNA of a first part of the ligands being complementary to bases of the single-strand DNA or RNA of a second part of the ligands and, during the method, binding to the complementary bases (preferably forming a Y-shape, in particular as illustrated in FIG. 6), a ligase being added during the method, which ligase ligates chemically covalently the further single-strand DNA or RNA of the first part of the ligands to the further single-strand DNA or RNA of the second part of the ligands.

A ligation of both further DNAs or RNAs hence takes places only if the result is hybridisation of the respective bases, i.e. if the total complex is sufficiently stable. It is advantageous with this embodiment however that once formation of a complex has taken place it is "stored" by the chemically covalent ligation of both further DNAs or RNAs. In other words, the ligated further DNAs or RNAs accumulate during the method if the basis for ligation thereof has been stable formation of the total complex. In this way, a clear increase in sensitivity of the method can be achieved, especially if the accumulated, ligated DNA or RNA can be further amplified via known methods (PCT, RT-PCR). As a result, also very small concentrations of ligands can be used in this way or high-affinity ligands can be identified even in the case of very small receptor concentrations.

In the above-cited embodiment, in the case of a single-strand DNA or RNA of a first part of the ligands,
i) which has bonded the ligand at the 5' end thereof, can have the bases, which are complementary to the bases of the single-strand DNA or RNA of a second part of the ligands, at the 5' end thereof, and the 2 to 10 bases of the further single-strand DNA or RNA, which are complementary to bases of the single-strand DNA or RNA of a second part of the ligands, can be disposed at the 3' end of the further single-strand DNA or RNA; or
ii) which has bonded the ligand at the 3' end thereof, can have the bases, which are complementary to the bases of the single-strand DNA or RNA of a second part of the ligands, at the 3' end thereof, and the 2 to 10 bases of the further single-strand DNA or RNA, which are complementary to bases of the single-strand DNA or RNA of a second part of the ligands, are disposed at the 5' end of the further single-strand DNA or RNA.

By means of this specific arrangement of the respective complementary bases, the formation of a Y-structure is assisted, which in turn increases the efficiency of the ligation of the two further single-strand DNAs or RNAs by the ligase.

Furthermore, a microfluidic device for implementing the method according to the invention is provided. The device comprises:
a) a container for receiving immobilised receptor, the container having an access with valve which serves for injection of ligands of a library and for isolation of ligand-receptor complexes, and the container having an inlet and an outlet for a fluid pipe;
b) a fluid pipe which is connected to an inlet and an outlet of the container and which has an outlet with valve at one place;
c) a heating device which is disposed in a first region of the fluid pipe; and
d) a cooling region which is situated in a second region of the fluid pipe, different from the first.

In the microfluidic device, the heating of ligands in solution and the selection of ligands which are bonded to immobilised receptor can take place locally separated from each other and hence thermal damage to the receptor (e.g. protein denaturation) can be prevented. The container can hereby retain immobilised receptor and prevent immobilised receptor from passing into the fluid pipes. Preferably, the container has hence filters which prevent passage of immobilised receptor into the fluid pipe.

In a preferred embodiment, the cooling region of the device has a cooling device and/or is disposed in the region of the outlet with valve.

The device can have a pump which is disposed such that it can pump a liquid through the fluid pipe. In particular, the container of the device can have filters which prevent passage of immobilised receptor into the fluid pipe.

The microfluidic device can be characterised in that the container and/or the fluid pipe comprises a dynamic, self-assembling chemical library according to the invention (see below).

Furthermore, a chemical library which comprises ligands is provided, which ligands have a single-strand DNA or RNA with a base length of more than 2 bases which are bonded chemically covalently to a ligand. The library is characterised in that 2 to 10 bases of the single-strand DNA or RNA of a first part of the ligands are complementary to bases of the single-strand DNA or RNA of a second part of the ligands.

Only 3 to 9 bases, preferably only 4 to 8 bases, particularly preferably only 5 to 7 bases, of the single-strand DNA or RNA of a first part of the ligands can hereby be complementary to the single-strand DNA or RNA of a second part of the ligands.

The length of the DNA or RNA of the first part of the ligands and/or second part of the ligands can be at least 20 bases, preferably at least 40 bases, particularly preferably at least 100 bases, in particular at least 200 bases.

In a preferred embodiment, the first and/or second part of the ligands constitutes more than 20%, preferably more than 30%, particularly preferably more than 40%, in particular 50%, of the total quantity of the ligands of the library. The first part of the ligands L preferably has L different ligands and the second part of the ligands preferably has L different ligands so that the library has $L^2$ different ligand complexes.

The ligands of the library can comprise a molecule selected from the group consisting of protein, peptide, lipid, carbohydrate, dsDNA, ssDNA, dsRNA and ssRNA, aptamer, organic molecule with a molecular mass≤200 kDa, preferably ≤100 kDa, particularly preferably ≤10 kDa, in particular ≤3 kDa, or consist thereof.

The single-strand
i) DNA can comprise adenine, thymine, guanine and/or cytosine; and/or
ii) RNA can comprise adenine, uracil, guanine, cytosine and/or inosine.

The library can be characterised in that the single-strand DNA or RNA of the ligands of the library is hybridised respectively in regions to form a complementary base sequence of a further single-strand DNA or RNA, 2 to 10 bases of a first further single-strand DNA or RNA of a first part of the ligands being complementary to bases of the second single-strand DNA or RNA of a second part of the ligands.

The single-strand DNA or RNA of a first part of the ligands,
i) which has the ligand at the 5' end thereof, can have the bases which are complementary to the bases of the single-strand DNA or RNA of a second part of the ligands, at the 5' end thereof, and the 2 to 10 bases of the further single-strand DNA or RNA, which are complementary to bases of the second single-strand DNA or RNA of a second part of the ligands, are disposed at the 3' end of the further single-strand DNA or RNA; or
ii) which has the ligand at the 3' end thereof, can have the bases which are complementary to the bases of the single-strand DNA or RNA of a second part, at the 3' end thereof, and the 2 to 10 bases of the further single-strand DNA or RNA, which are complementary to bases of the single-strand DNA (9) or RNA of a second part of the ligands, can be disposed at the 5' end of the further single-strand DNA or RNA.

Finally, the use of the chemical library according to the invention for selective and sensitive identification of high-affinity ternary ligand-receptor complexes is proposed.

The subject according to the invention is intended to be explained in more detail with reference to the subsequent Figures without wishing to restrict said subject to the specific embodiments illustrated here.

Figure 1:
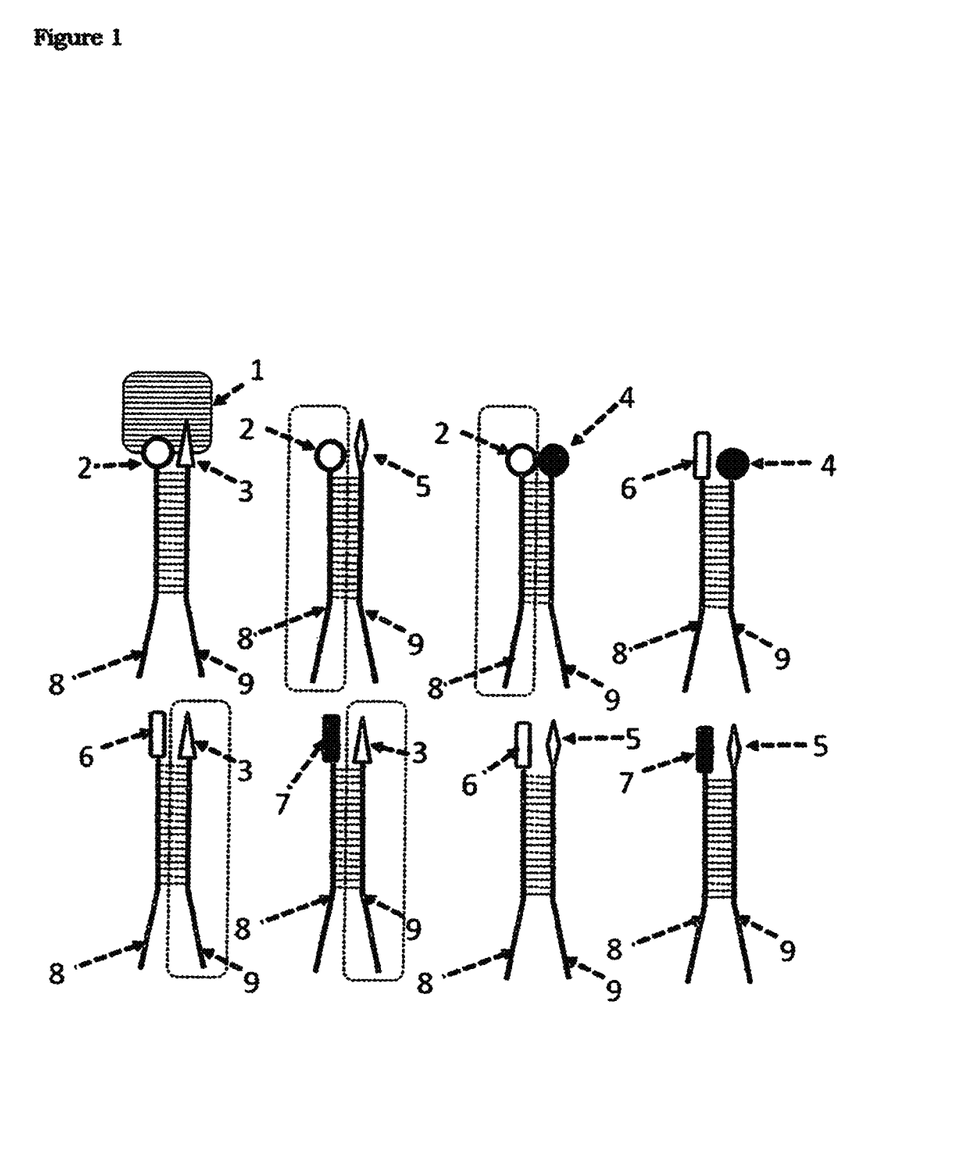

FIG. 1 shows a large number of different ligands 2, 3, 4, 5, 6, 7 of a chemical library and at least one receptor 1. The ligands 2, 3, 4, 5, 6, 7 are bonded respectively chemically covalently to a single-strand DNA 8, 9, the single-strand DNA 8, 9 having a base length of more than 10 bases. The single-strand DNA 8, 9 codes respectively for the respective ligand, to which it is bonded, via the base sequence thereof. In this embodiment, 18 bases of the single-strand DNA 8 of a first part of the ligands 2, 6, 7 are complementary to bases of the single-strand DNA 9 of a second part of the ligands 3, 4, 5 (see broken line between the single-strand DNAs 8, 9). Here only a specific ligand pair (formed by the ligands of the reference numbers 2 and 3) binds with high affinity to the receptor 1. Other ligand pairs (formed by the ligands of the reference numbers 4, 5, 6, 7) bind weakly as far as not at all to the receptor 1. As a result of the high number of complementary bases between the single-strand DNAs 8, 9 of two ligands 2, 3, 4, 5, 6, 7, the ligand complexes are stabilised, which causes high sensitivity during use thereof in a detection method. In order to achieve a dynamic of the hybridisation and dissociation, permanent heating (dissociation) and cooling (reassociation or hybridisation), i.e. an energy supply, is necessary.

Figure 2:
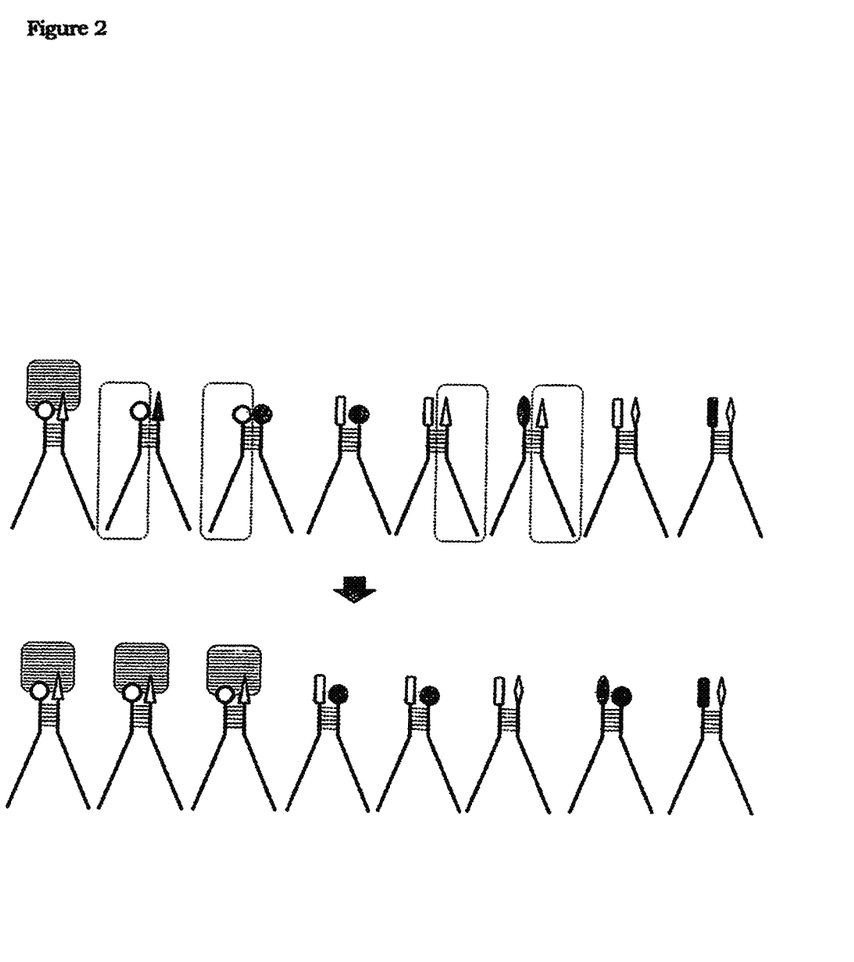

FIG. 2 shows an illustration corresponding to FIG. 1, with the difference that, in this embodiment, only 6 bases of the single-strand DNA of a first part of the ligands are complementary to bases of the single-strand DNA or RNA of a second part of the ligands (otherwise the molecules and references are identical to FIG. 1). As a result of the lower number of complementary bases, the advantage arises that the association (hybridisation) of two ligands is highly dynamic already at room temperature (15° C. to 30° C.), i.e. permanent hybridisation and dissociation takes place. The high-affinity binding to receptor, present in the case of specific ligand pairs, restricts the dissociation of these ligand pairs, as a result of which complexes made of receptor and high-affinity ligand pairs are populated for longer, "accumulate" in the course of time and finally are populated more highly in the equilibrium. It is advantageous in this embodiment that the dynamic of the association and hybridisation takes place at room temperature, i.e. in contrast to the embodiment of FIG. 1, no thermal energy need be supplied. The disadvantage of this embodiment is lower sensitivity than in the embodiment in FIG. 1 since the lower number of base pairs (6 instead of 18) makes the ligand complex and hence the complex of ligands with the receptor more unstable, as a result of which the latter is populated less highly in the equilibrium than in the embodiment in FIG. 1.

Figure 3:
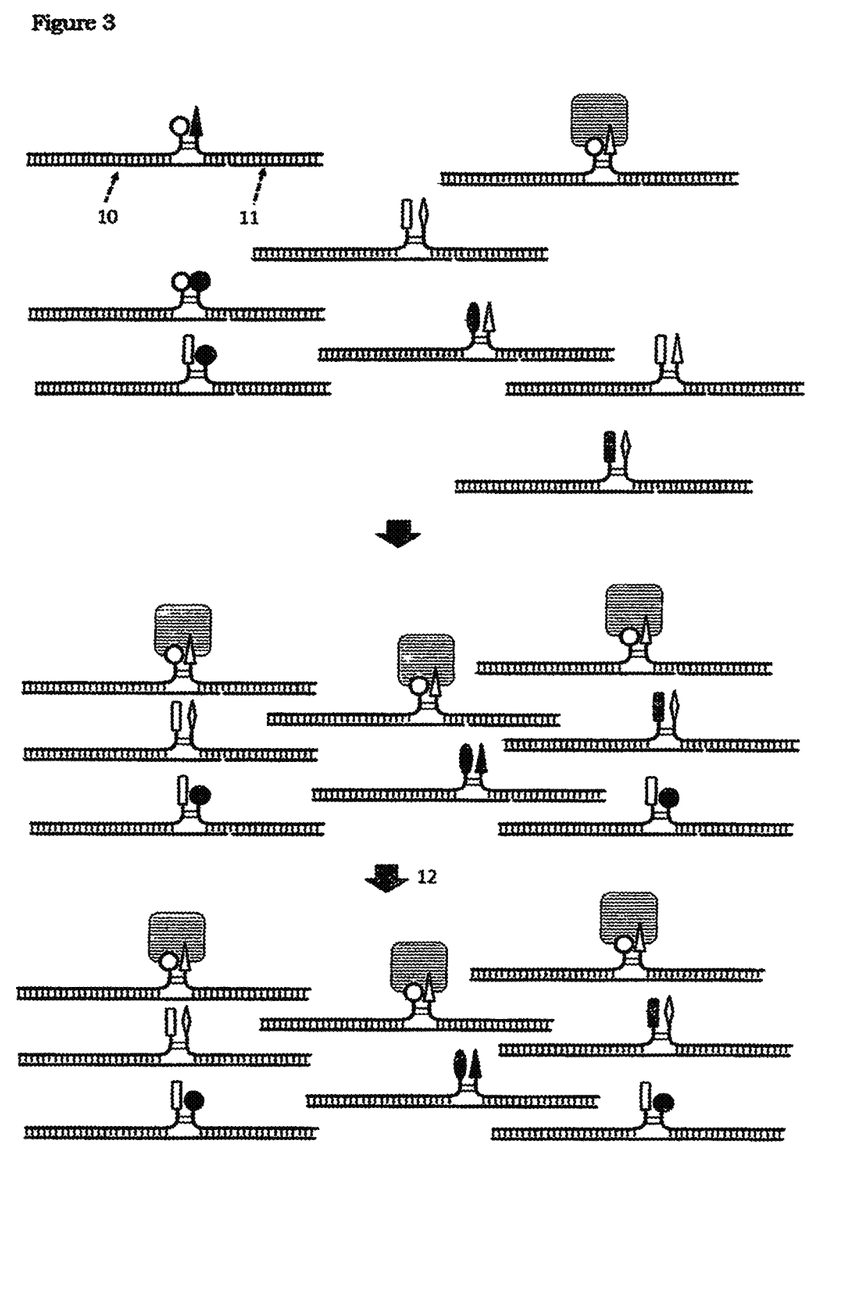

FIG. 3 clarifies, via a reaction equation, how the high-affinity ligand pairs "accumulate" as complex with the receptor in the course of time (see first arrow above). In addition to the molecules mentioned already from FIG. 1 and FIG. 2, the ligand pairs also have a single-strand DNA 10, 11 which is complementary respectively also to the single-strand DNA bonded covalently to the ligand (otherwise the molecules and references are identical to FIG. 1). This additional single-strand DNA 10, 11 can be generated for example via suitable primers and a PCR reaction. The lower arrow 12 symbolises a ligation reaction (e.g. by the addition of a ligase enzyme which leads to the two additional single-strand DNAs 10, 11 being ligated to each other chemically covalently. The advantage hereby is that the ligated DNA fragment is coded respectively for a specific ligand pair via the base sequence thereof, which pair can be hence identified easily via DNA sequencing.

Figure 4:
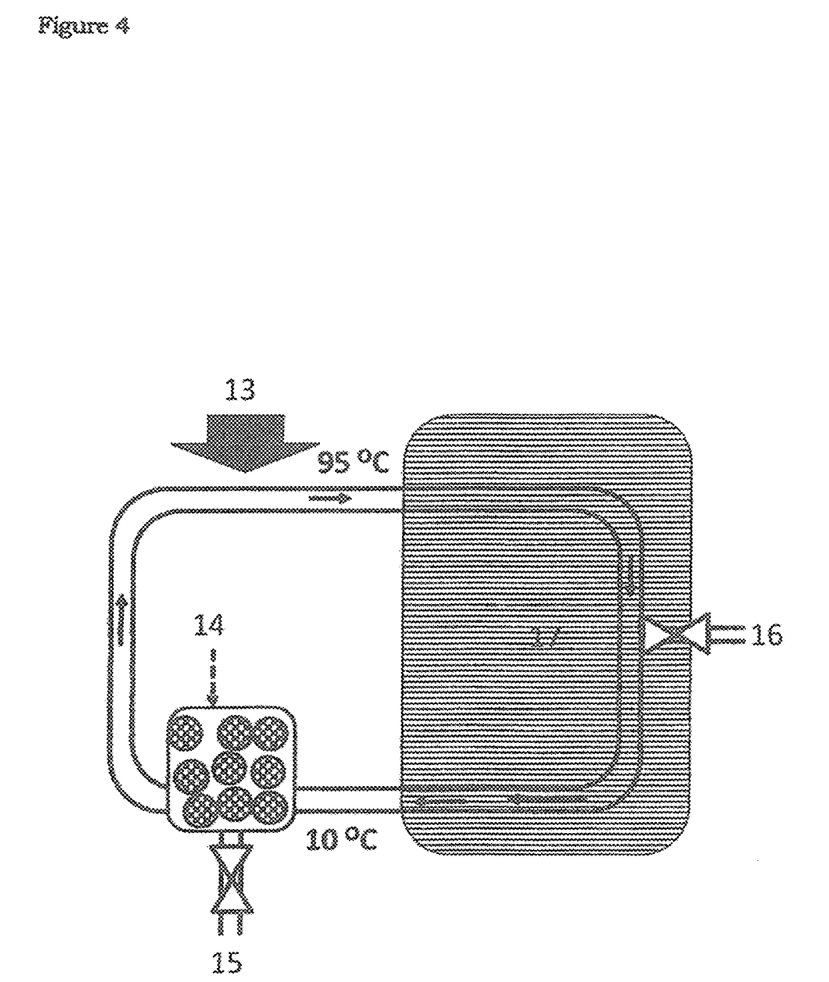

FIG. 4 describes a microfluidic device according to the invention. Immobilised receptor, which was filled into the container via the opening 15 with valve is situated in a container 14. The container 14 is connected on the one side and on the other side to a pipe, through which a liquid can be guided. The pipe is in a zone which can be heated. Heating can be effected via an IR radiator as heating source 13. Furthermore the device has a cooling zone 17. Optionally, this zone comprises a cooling device. In addition, the pipe, here in the cooling region 17, has an outlet 16 with a valve out of which liquid with (free) ligands can be removed and can be supplied for analysis. In addition, after a specific incubation time, immobilised receptor charged with high-affinity ligands can be removed via the opening 15.

Figure 5:
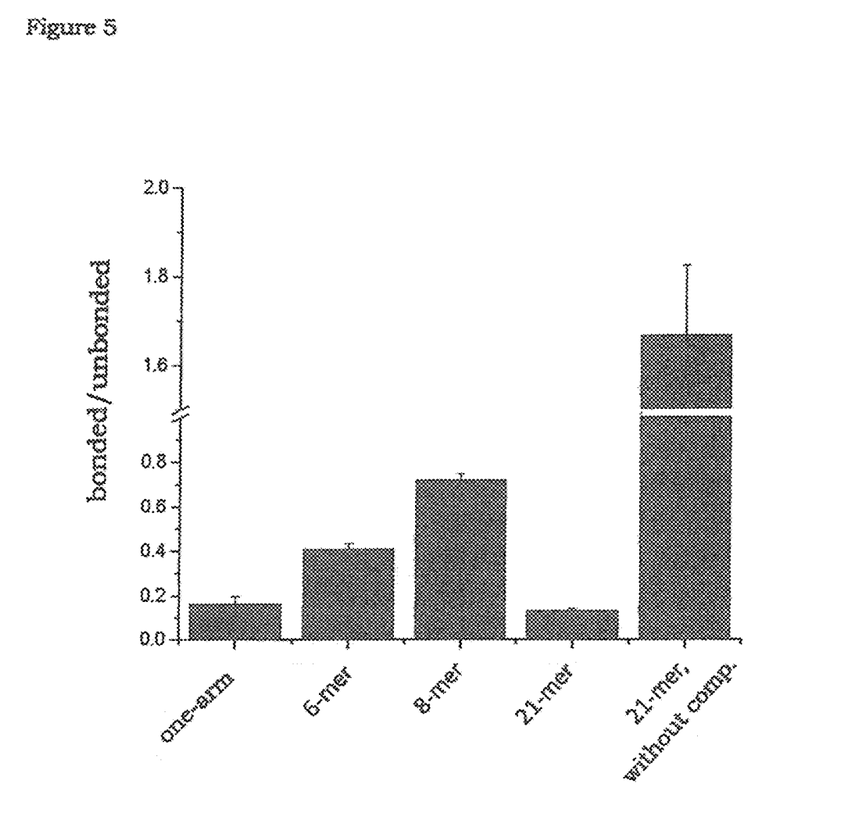

FIG. 5 shows the result of an experiment which verifies the effectiveness of the method according to the invention. Iminobiotin was used as ligand which has been bonded chemically covalently respectively to ssDNA (=im-ssDNA). The im-ssDNA was divided, in equal parts, into a first part of im-ssDNA1 and a second part of im-ssDNA2, im-ssDNA1 and im-ssDNA 2 having a different number of bases which are complementary to each other according to the experiment (e.g. 6 complementary bases in the case of "6-mer"). Im-ssDNA1 was coupled chemically covalently to the fluorescent dye Cy5 in order to enable, on the one hand, detection and quantification of free im-ssDNA1 or the free binary complex made of im-ssDNA1 and im-ssDNA2 without receptor and, on the other hand, detection of the ternary im-ssDNA1·im-ssDNA2·receptor complex. As receptor, immobilised streptavidin was used and, as solution, an aqueous buffer with pH 9.2 was used. The Figure shows the ratio of the quantity of ligand-receptor complex to ligands not bonded to the receptor ("bonded/unbonded" on the y-axis) under competitive conditions, i.e. in the presence of iminobiotin-free ssDNA (ssDNA) as example of a non-affine ligand (see "one-arm", "6-mer", "8-mer" and "21-mer" on the x-axis) or non-competitive conditions, i.e. without the presence of competitive ssDNA ("21-mer, no comp." on the x-axis).

Apart from in the non-competitive experiment ("21-mer, no comp." on the x-axis), the iminobiotin-free ssDNA was present in the solution in 300 times excess. In the experiment with the title "one-arm" (also a 6-mer), only im-ssDNA1 was present, i.e. no im-ssDNA2, so that no binary ligand complexes were able to be formed. The "one-arm" experiment hence shows the binding ratio for a monomeric iminobiotin to streptavidin. In direct comparison to the "6-mer" experiment, it becomes clear that, under the tested competitive conditions with dimeric iminobiotin (=binary ligand complex), the binding equilibrium is displaced clearly in the direction of ligand-receptor complex. This effect is more clearly pronounced by the higher stabilisation due to hybridisation of 8 base pairs in the "8-mer" experiment. If the number of complementary bases rises further however (e.g. here 21 complementary bases in the "21-mer" experiment), then the quantity of obtained ligand-receptor complex falls to a value which corresponds approximately to the value of the "one-arm" experiment.

This observation can be explained by the fact that the Cy5-labelled iminobiotin-bonded ssDNA (im-ssDNA1) is "trapped" in low-affinity binary complexes with iminobiotin-free ssDNA (ssDNA) and therefore can no longer bind to complementary Cy5-free, but iminobiotin-containing, ssDNA (im-ssDNA2). This effect is observed therefore only in the "21-mer" experiment since here a formed im-ssDNA1·ssDNA complex is so stable that, at room temperature (without further energy supply), dissociation of this complex in practice no longer takes place. In the case of a number of complementary bases of 6 and 8 bases ("6-mer" or "8-mer"), this effect does not however occur since here the formation of the im-ssDNA1·ssDNA complex is not static, but is dynamic and hence, in the case of this lower number of complementary bases, an iminobiotin-bonded ssDNA (im-ssDNA1) which is "blocked" by ssDNA becomes free again and can react with a further iminobiotin-bonded ssDNA (im-ssDNA2) to form a high-affinity binary complex. Consequently, in the case of a number of base pairs of 6 and 8, an "accumulation" of complexes made of receptor (here streptavidin) and high-affinity ligand pairs (here a pair of two iminobiotin-molecules) is achieved at room temperature, as a result of which this method is superior, with respect to sensitivity, to a static method. The sensitivity can be increased by a number of 21 base pairs being used and being alternately heated (dissociation) and cooled (hybridisation), i.e. energy is supplied.

FIG. 6 shows a Y-form which the total complex adopts in a preferred embodiment of the invention. The first ligand 2 which is bonded chemically covalently to the first single-strand DNA 8 has a portion 18 which codes for the first ligand 2. The second ligand 3 which is bonded chemically covalently to the second single-strand DNA 9 has a portion 19 which codes for the second ligand 3. Here, six bases of the first single-strand DNA 8 are complementary to six bases of the second single-strand DNA 9 and, during the method, can form base pairs 20 (see the lines between the single-strand DNAs 8, 9). Furthermore, the first single-strand DNA 8, in this embodiment, is hybridised in regions (here: at the 3' end) with a first additional single-strand DNA 10. The first additional single-strand DNA 10 is characterised in that it comprises an "overhang" of two to twelve bases (here: five bases, located at the 3' end thereof) which are complementary to two to twelve bases of the second single-strand DNA 9 (here: five bases) and which, with the complementary bases, can form base pairs 20 during the method (see the lines between the additional first single-strand DNA 10 and the second single-strand DNA 9).

If the second ligand 3 is hybridised via the second single-strand DNA 9 in regions with a suitable second additional DNA 11, then formation of the total complex is effected (here: in Y-form) such that the first additional DNA 10 is brought together with the second additional DNA 11 such that they can be ligated chemically covalently via addition of a ligase enzyme. If a ligase enzyme is added in the method, then it is achieved that ligation products of both single-strand additional DNAs 10, 11 which code for high-affinity ligand complexes accumulate in the course of the method. As a result, the sensitivity of detection thereof rises. Since the accumulation product concerns DNA, this can be amplified even further (e.g. by PCR), as a result of which the sensitivity of the method is increased again. In addition, sequencing of the ligated DNA allows a rapid conclusion to be made with respect to the two ligands 2, 3 since the ligated DNA has the portions 18, 19 which codes for both ligands 2, 3.

The invention claimed is:

1. A method for production and identification of ternary ligand-receptor complexes comprising a first ligand, a second ligand different than the first ligand, and one receptor, comprising the steps of:

(a) combining: (i) ligand complexes with (ii) the one receptor in a solution, wherein the ligand complexes comprise a plurality of first ligands of a chemical library, wherein each first ligand of the chemical library is different one from another, each of the first ligands being chemically covalently bonded to a first single-strand DNA or first single-strand RNA, and a plurality of second ligands of a chemical library, wherein each second ligand of the chemical library is different one from another, each of the second ligands being chemically covalently bonded to a second single-strand DNA or second single-strand RNA having more than 10 bases complementary to bases of the first single-strand DNA or first single-strand RNA, such that the first ligands are hybridized with the second ligands to form the ligand complexes via hybridization of the more than 10 complementary bases of the first single-strand DNA or first single-strand RNA with second single-strand DNA or second single-strand RNA, respectively;

(b) incubating the solution for a specific period of time and at a temperature of 1° C. to 50° C., such that at least one ligand complex binds to the one receptor to produce a ternary ligand-receptor complex, wherein each first ligand of the ligand complex and each second ligand of the ligand complex is separately bound to the one receptor to form the ternary ligand-receptor complex;

(c) spatially separating the ternary ligand-receptor complexes from the ligand complexes in solution to produce a solution comprising the ligand complexes formed in step (a) that did not bind to the one receptor;

(d) identifying the ternary ligand-receptor complexes spatially separated in step (c);

(e) dissociating the ligand complexes in the solution produced in step (c) that did not bind to the one receptor by increasing the temperature of the solution of step (c) to a temperature of 35° C. to 95° C. to break the non-covalent bonds between the first single-strand DNA or first single-strand RNA of the first ligand and the second single-strand DNA or second single-strand RNA of the second ligand to form dissociated free first ligands and dissociated free second ligands, wherein more than 10 bases of the first single-strand DNA or first single-strand RNA associated with the dissociated free first ligands are complementary to bases of the second single-strand DNA or second single-strand RNA associated with the free second ligands;

(f) hybridizing the dissociated free first ligands comprising first single-strand DNA or first single-strand RNA formed in step (e) with the dissociated free second ligands comprising second single-strand DNA or second single-strand RNA formed in step (e) to form further ligand complexes;

(g) incubating the solution of step (f) with the same one receptor of step (a) for a specific period of time and at a temperature of 1° C. to 50° C. to produce further ternary ligand-receptor complexes; and (h) identifying the ternary ligand-receptor complexes produced in step (g), thereby identifying high-affinity complexes comprising two ligands and one receptor.

2. The method according to claim 1, wherein steps (e) to (g) are repeated at least once.

3. The method according to claim 1, wherein at least 20 bases of the single-strand DNA or the single-strand RNA of the first ligands are complementary to the second single-strand DNA or the second single-strand RNA of the second ligands.

4. The method according to claim 1, wherein the length of the single-strand DNA or single-strand RNA of the first ligands and/or the length of the single-strand DNA or single-strand RNA of the second ligands is at least 20 bases.

5. The method according to claim 1, wherein the plurality first ligands in the chemical library have a number L of different ligands and the plurality of second ligands in the chemical library have a number M of different ligands such that L×M different ligand complexes are formed.

6. The method according to claim 1, wherein the solution is incubated in at least one of steps (b) and (g) at a temperature of 5° C. to 37° C.

7. The method according to claim 1, wherein the solution is incubated in at least one of steps (b) and (g) for a period of time of 0.1 to 48 hours.

8. The method according to claim 1, wherein the receptor is immobilized on a substrate selected from the group consisting of glass, ceramic, biopolymer, sepharose, synthetic polymer, and hydrogel.

9. The method according to claim 1, wherein the receptor comprises a molecule selected from the group consisting of a protein, a DNA, an RNA, a cell, an organic molecule with a molecular mass ≤200 kilo-Daltons, and combinations thereof.

10. The method according to claim 1, wherein at least one of the first ligands and at least one of the second ligands comprises a molecule selected from the group consisting of protein, peptide, lipid, carbohydrate, single-strand DNA, double-strand DNA, single-strand RNA, double-strand RNA, aptamer, and organic molecule with a molecular mass ≤200 kilo-Daltons.

11. The method according to claim 1, wherein the ternary ligand-receptor complexes are identified via an analytical method selected from the group consisting of mass spectrometry (MS), high performance liquid chromatography (HPLC), gas chromatography (GC), infrared (IR) spectroscopy, and DNA sequencing.

12. The method according to claim 1, wherein the first single-strand DNA or the first single-strand RNA in the first ligands and/or the second single-strand DNA or the second single-strand RNA in the second ligands comprises a base sequence which codes for the chemically covalently-bonded first ligands or the chemically covalently-bonded second ligands.

* * * * *